United States Patent [19]

Burvee

[11] Patent Number: 4,698,724
[45] Date of Patent: Oct. 6, 1987

[54] DISPOSABLE, ELECTRICALLY CONDUCTIVE BODY GROUNDING STRAP

[75] Inventor: Richard W. Burvee, Austin, Tex.

[73] Assignee: Minnesota Mining and Manufacturing Company, St. Paul, Minn.

[21] Appl. No.: 944,256

[22] Filed: Dec. 18, 1986

[51] Int. Cl.$^4$ .............................................. H05F 3/02
[52] U.S. Cl. .................................................... 361/220
[58] Field of Search ............... 361/219, 220, 212, 223, 361/224; 174/6

[56] References Cited

U.S. PATENT DOCUMENTS

| | | | |
|---|---|---|---|
| 2,955,234 | 10/1960 | Price | 361/223 |
| 3,857,397 | 12/1974 | Brosseau | 361/220 X |
| 4,398,277 | 8/1983 | Christiansen et al. | 361/220 |
| 4,577,256 | 3/1986 | Breidegam | 361/220 |

Primary Examiner—L. T. Hix
Assistant Examiner—Brian W. Brown
Attorney, Agent, or Firm—Donald M. Sell; James A. Smith; William D. Bauer

[57] ABSTRACT

An electrically conductive strap having a distal end adapted to be secured to an object and having a proximate end adapted to be coupled to electrical ground. The strap has an elongate strip of electrically conductive material being flexible in at least one dimension. The material has an object contacting portion at the distal end, a lead portion between the distal end of the proximate end and a ground contacting portion at the proximate end. An adhesive securing mechanism is provided at the object contacting portion of the elongate strip of electrically conductive material to secure the material in electrical contact with the object. A ground contacting mechanism is provided at the ground contacting portion of the material to be able to couple the electrically conductive strap to electrical ground.

29 Claims, 9 Drawing Figures

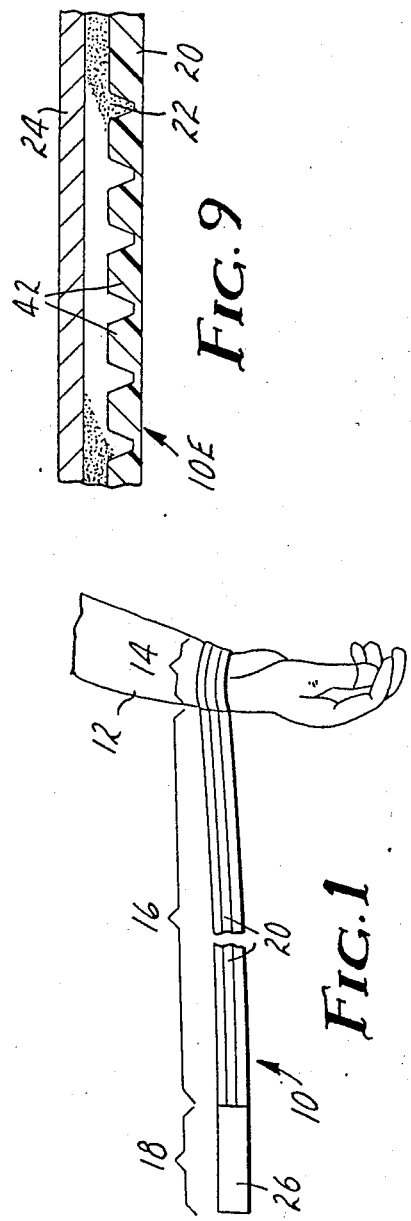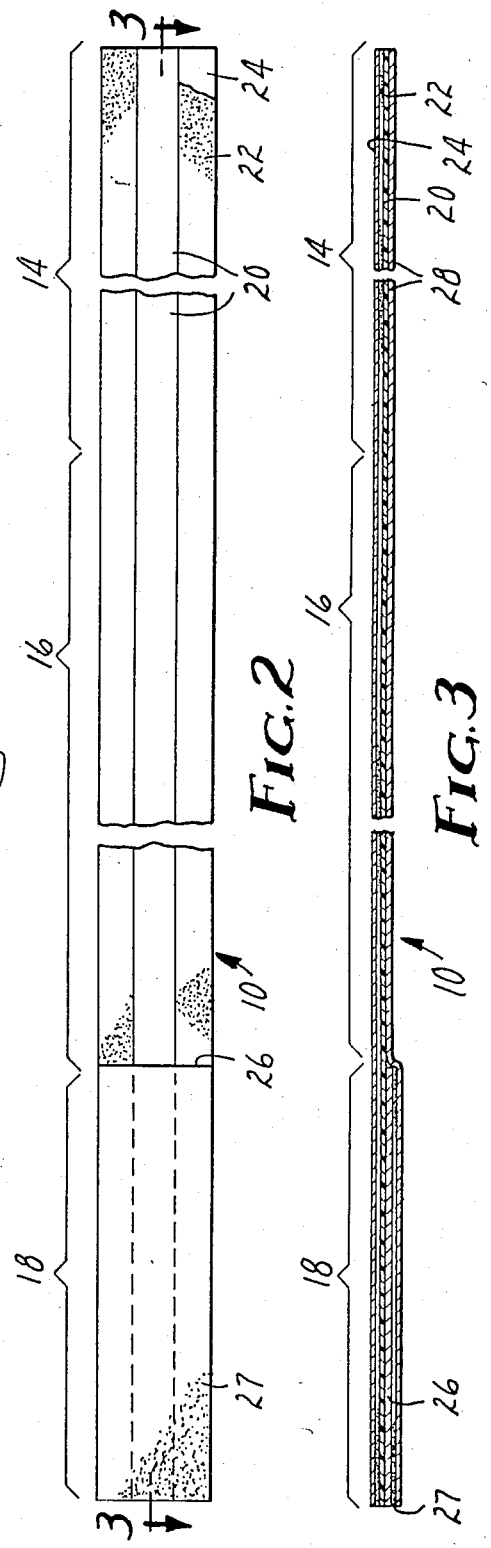

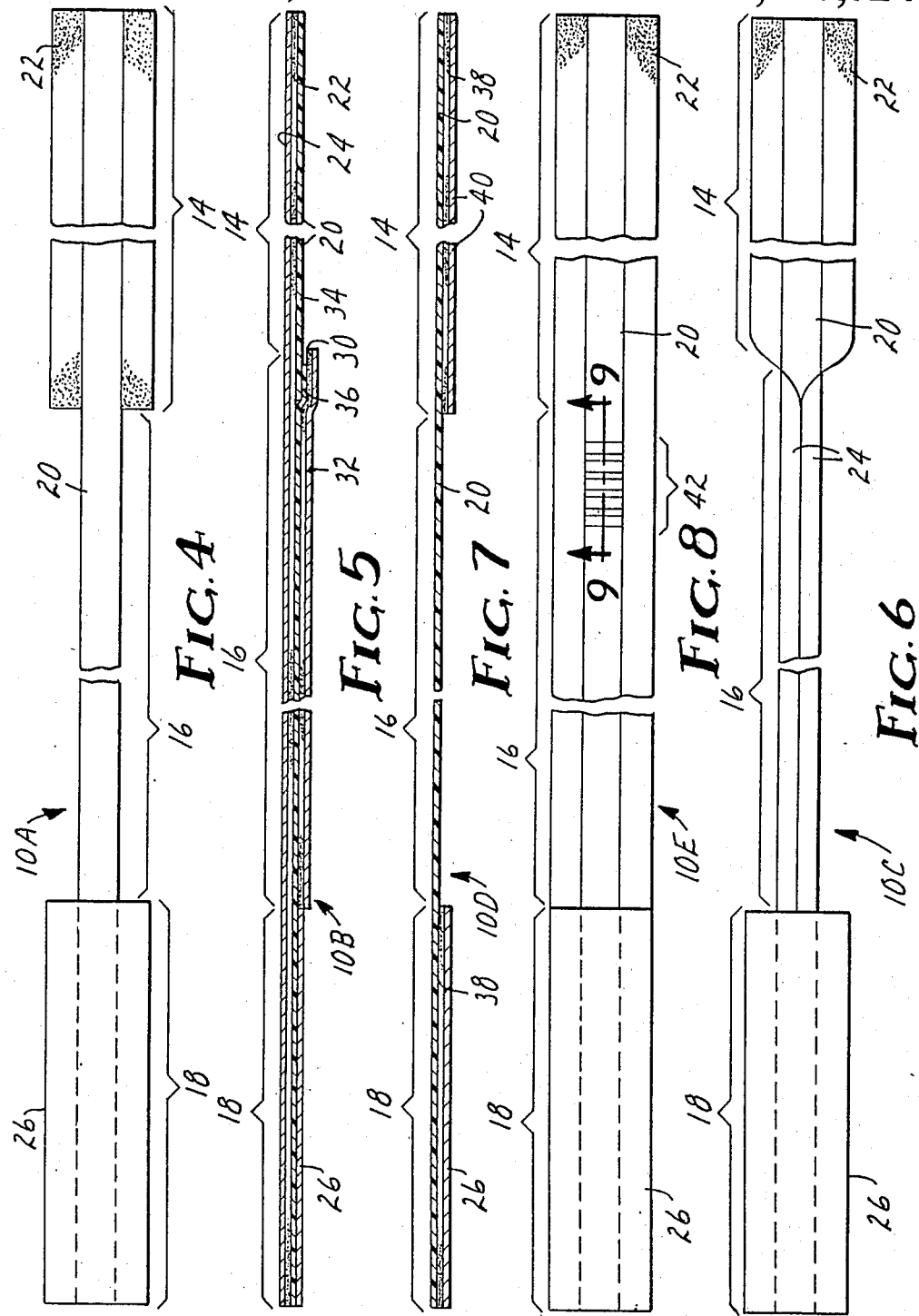

DISPOSABLE, ELECTRICALLY CONDUCTIVE BODY GROUNDING STRAP

BACKGROUND OF THE INVENTION

The present invention relates generally to electrically conductive body straps for the control of electrostatic charges.

Persons who are around electrostatic sensitive articles need to be protected from acquiring or retaining an electrostatic charge. A person who acquires and retains a buildup of an electrostatic charge and who comes near to or in contact with an electrostatic sensitive article, e.g., an integrated circuit or electronic device, may deliver a sudden electrical discharge through the article severely damaging or destroying it. One mechanism to protect such electrostatic sensitive article is to electrically ground the body of the person who may come near to or in contact with the articles. Electrically conductive body straps, typically contacting the wrist, are utilized to electrically couple to the body of the person. The conductive body strap may then be electrically connected to ground in order to drain to electrical ground any electrostatic charge existing or generated on the body of the person.

There are several examples of electrically conductive body grounding straps in existance.

One of these straps is the Model 2064 wrist strap manufactured by Minnesota Mining and Manufacturing Company (3M), St. Paul, Minn. The Model 2064 wrist strap consists of a Velostat (Velostat is a trademark of the 3M Company) strip held on the wrist with a band of nylon. Velostat conductive material is a carbon loaded conductive polymer. The operation of the wrist strap relies on the conductive polymer to conduct electrostatic charge via the individual's wrist to a ground cord secured to the wrist strap with an electrically conductive snap connection. The Model 2064 wrist strap relies on a hook and loop fastener system (e.g., Scotchmate, a trademark of the 3M Company, fastener) to secure the wrist strap to the wrist of the individual wearer.

A wrist strap manufactured by Semtronics Corporation, Peachtree City, Ga. is constructed from similar functional components. The Semtronics carbon loaded wrist strap also uses a black conductive plastic secured to the wrist with a hook and loop closure system.

A wrist strap manufactured by Simco, Lansdale, Pa. also uses a similar system. The entire band of the wrist strap is made of a nylon hook and loop fastener system. The Simco wrist strap has a carbon loaded conductive material secured to the inner surface of the hook and loop fastener. A snap connection is provided for a ground cord. The Simco wrist strap again relies on the conductive polymer for conducting the electrostatic accumulation on the individual to the snap connection and to the grounding cord. The Simco wrist strap relies on the hook and loop fastener to close the wrist strap on itself and thereby secure the strap to the wrist of the wearer.

A wrist strap manufactured by Wescorp of Mountainview, Calif. consists of a carbon loaded conductive fabric with a hook and loop fastener. The Wescorp wrist strap relies on the conductive fabric for the conduction of electrostatic charge from the individual instead of the conductive polymer as in the previous straps but again relies on the hook and loop fastener for the closure system.

A strap manufactured by Walter G. Legge Company, New York, N.Y. carrying the name "WRISTSTAT" uses a black nylon band with a hook and loop fastener. A conductive polymer is attached to the band with a metallic plate at a relatively narrow location around the strap. The conductive polymer also has a snap connection to a ground cord. The Legge wrist strap relies on the metal plate and the conductive polymer for conductivity and relies on the nylon band with the hook and loop fastener for the closure system.

The straps heretofore described are all very similar in nature. Almost all rely on a carbon loaded conductive polymer and the remainder on a carbon loaded fabric. All of the wrist straps rely on a hook and loop fastener for a closure system.

Wescorp also has a strap consisting of a metallic bead chain to which an electrical ground cord is slidably attached. The strap relies on the metallic beads for conductivity. Since it is worn loosely around the wrist, it can be made large enough to slip over the hand onto the wrist and, thus, no detachable closure is required. This strap, however, does not ensure proper electrical connection since the strap is not intimately in contact with the body (wrist) of the individual wearer.

Controlled Static Company, Santa Fe, Calif. manufactures a wrist strap known in the trade as a Fred strap. The strap is a metallic expansion band having a snap connection for an electrical ground cord. The band is reminiscent of a metallic expansion watchband. The band relies on the conductivity of the metal for the drainage of the accumulated electostatic charges and will expand, slip on the wrist over the hand and then fit relatively snug. However, the wrist strap suffers the disadvantage of a relatively low expansion ratio. The strap must be large enough to slip over the hand and small enough to fit snugly on the wrist.

Further, the two previous metallic straps also suffer another significant disadvantage since the highly conductive metallic surface is available at the outside surface of the wrist strap, there is a danger of accidental contact with a high voltage source and the resultant "welding" of the strap to that source preventing disengagement of the wearer from the high voltage source. It is for this reason that some electricians do not wear metallic rings, bracelets and other jewelry.

U.S. Pat. No. 4,398,277, Christiansen et al, assigned to 3M, describes an electrically conductive elastomeric fabric and wrist strap. In Christiansen et al, a knitted fabric with elastomeric yarns and electrically conductive yarns is secured in a clasp with a snap for a ground wire connection. The knitted fabric is extensible to slip over the hand and yet fits snugly on the wrist. This strap operates extremely well; however, the cost of construction, in particular the silver thread utilized in the electrically conductive yarn, mitigates against this strap being utilized in a onetime use disposable application.

U.S. Pat. No. 4,577,251, Breidegam, discloses an electrically conductive elastomeric wrist strap. The fabric contained in the strap is a stretch weave with stretched longitudinal conductive threads. The fabric is adjustably secured into a clasp to form a closed loop in circling the wrist of the wearer. A snap is provided for an electrical ground wire connection. The Breidegam strap is somewhat extensible to slip over the hand, it is then pulled tight and secured to fit snugly around the wrist. Again, the cost of construction of this strap mitigates against its onetime use disposable application.

The closure system on the strap described in U.S. Pat. No. 3,857,397, Broeseonis is formed with the end of the strap having an opening. The strap is placed around the wrist with the one end brought back through the opening on the other end and snugged tight up against the wrist and secured in that position with a hook and loop fastener system. The opening in the end of the strap to bring the other end of the strap through makes it cumbersome to use on the wrist. The cost of construction mitigates against a onetime use disposable application.

A disadvantage of all the previous disclosed straps are that all of these straps are relatively expensive. Wrist straps must be inventoried and stored at the point of use by the potential wearer who comes in close contact with electrostatic sensitive articles. The wrist straps once used and worn must be maintained to ensure their proper functioning. Over a period of time, the electrical performance of any strap may deteriorate and, thus, the straps must be repeatedly tested to ensure for proper functionality. The cost of inventorying, storing and testing such wrist straps may limit the applications for which they can be used.

SUMMARY OF THE INVENTION

The present invention provides a functional, inexpensive, compact wrist strap which is suitable for a onetime use disposable application. Until the present invention, wrist straps were relatively expensive limiting their applications for usefulness. The present invention provides a disposable onetime use wrist strap which could be packaged with an electrostatic sensitive device at the point of sale for use by the buyer of such device during its installation. For example, a computer circuit board intended for consumer sale could be packaged with a disposable electrically conductive body strap. The home computer user could then remove the strap from the package, properly connect the strap and be electrostatically protected when he removes the board from the package and installs it in his computer. Due to the cost and durability of previous strap designs, this application typically has gone without electrostatic protection.

The present invention provides an electrically conductive strap having a distal end adapted to be secured to an object and having a proximate end adapted to be coupled to electrical ground. The strap has an elongate strip of electrically conductive material being flexible in at least one dimension. The material having an object contacting portion at the distal end and having a lead portion between the distal end and the proximate end and having a ground contacting portion at the proximate end. The strap has a securing means affixed to the object contacting portion of the material for being able to adhesively secure the material to the object with the material and electrical contact with the object. The strap further has a ground contact mechanism at the ground contacting portion of the material enabling the strap to be coupled to electrical ground. In one embodiment, the elongate strip of electrically conductive material is substantially continuous and of the same type along the object contacting and lead portions of the material. In one embodiment, the elongate strip of electrically conductive material is an electrically conductive plastic and is preferably constructed from a carbon loaded plastic. In a preferred embodiment of the electrically conductive strap, incorporates a resistance mechanism in the lead portion for providing a discrete location which has a higher value of electrical resistance per unit length and the value of the electrical resistance per unit length of the remainder of the elongate strip of electrically conductive material. In one embodiment, the adhesive securing mechanism is an adhesive coated tape having a width greater than the width of the body contacting portion of the material the adhesive coated tape being applied adhesive coated side toward the material to the body contacting portion of the material. In other embodiments, a second adhesive coated tape is applied opposite the first adhesive coated tape in the lead portion of the electrically conductive material or the first adhesive coated tape is at least twice the width of the electrically conductive material and it is folded over and applied to both the sides of the electrically conductive material in the lead portion.

BRIEF DESCRIPTION OF THE DRAWINGS

The foregoing advantages, construction and operation of the present invention will become more apparent from the following description and accompanying drawings in which:

FIG. 1 is a perspective view of a strap of the present invention connected to the wrist of a person;

FIG. 2 illustrates a bottom plan view of a strap of the present invention with parts thereof removed;

FIG. 3 illustrates a sectional view taken along line 3—3 of FIG. 2 of a strap of the present invention;

FIG. 4 illustrates a bottom view of an alternative embodiment of a strap of the present invention having only an elongate conductor in the lead portion;

FIG. 5 illustrates a sectional view of an alternative embodiment of a strap of the present invention having dual sided tape applied and a noncontinuous elongate conductor;

FIG. 6 illustrates a bottom view of an alternative embodiment of the strap of the present invention having tape folded over the lead portion of the elongate conductor;

FIG. 7 illustrates a sectional view of an alternative embodiment of a strap of the present invention utilizing a conductive adhesive as the securing mechanism;

FIG. 8 illustrates a bottom view of an alternative embodiment of a strap of the present invention having an integral resistance built into the elongate conductor; and FIG. 9 illustrates a sectional view taken along line 9—9 of FIG. 8 of the resistance portion of the elongate conductor of the strap of FIG. 8.

DETAILED DESCRIPTION OF THE PREFERRED EMBODIMENTS

FIG. 1 illustrates a perspective view of the electrically conductive body strap 10 connected to the wrist 12 of a person. As shown, the strap has an object or body contacting portion 14 which is wrapped around and adhesively secured to the wrist 12, a lead portion 16 and a ground contacting portion 18. The length of the electrically conductive strap 10 in the body contacting portion 14 should be long enough to substantially wrap around the wrist 12, or other bodily part to which the strap 10 is to be connected, to which the body contacting portion 14 is adhesively secured. In an alternative embodiment, the body contacting portion 14 need not wrap around the wrist 12 or other bodily part but merely be long enough to be securly adhesively fastened to the body part and to provide adequate electrical connection to the body part. The length of the lead portion 16 of the electrically conductive strap 10 is indeterminate. The purpose of the lead portion 16 is to enable the wearer to have some movement in order to accomplish the task for which he is electrostatically protected. In a typical environment, the length of lead portion 16 would be approximately 2 to 5 feet (0.6 to 1.5 meters). Ground contacting portion 18 need only be made large enough to enable appropriate electrical connection from the electrically conductive strap 10 either directly to an electrical ground or to another electrical ground strap which in turn will be connected to electrical ground. In a typical environment, the length of ground contacting portion 18 will be approximately 2 to 4 inches (5 to 10 centimeters). Electrically conductive body strap 10 should be flexible in at least one dimension. As envisioned the electrically conductive body strap 10 is a relatively flat strip of material or combination of layered materials which provide flexibility to enable the body contacting portion 14 to be wrapped around the wrist 12.

FIGS. 2 and 3 illustrate bottom and sectional views, respectively, of the electrically conductive body strap 10. Electrically conductive body strap again has a body contacting portion 14, a lead portion 16 and a ground portion 18. An elongate, flat, flexible electrical conductor 20 runs the length of the electrically conductive body strap 10 through body contacting portion 14, lead portion 16 and ground portion 18. In a preferred embodiment, an elongate strip of electrically conductive material 20 is a one mil to five mil (0.03 to 0.13 millimeters) thick strip of carbon loaded polyethylene approximately three-eighths to one-half inch (0.95 to 1.3 centimeters) wide and preferably constructed from Velostat carbon loaded polyethylene available from Minnesota Mining and Manufacturing Company, St. Paul, Minn. It is preferred that the elongate strip of electrically conductive material 20 have an overall resistance over the length of the electrically conductive body strap 10 of not more than about 1 megohm. Affixed to the top side of the elongate strip of electrically conductive material 20 is an adhesive 22 coated tape 24. The adhesive coated tape 24 is wider than the elongate strip of electrically conductive material 20 and in a preferred embodiment it is approximately 3 times the width of material 20 or approximately 1.5 inches (4 centimeters) wide. Adhesive coated tape 24 provides a top insulative surface to the electrically conductive body strap 10. Adhesive 22 secures tape 24 to material 20 as well as secures the electrically conductive body strap 10 to the body of the person. In the embodiment shown in FIGS. 2 and 3, the electrically conductive body strap is constructed identical in both the body contacting portion 14 and lead portion 16. A metallic foil 26, preferably copper approximately 3 mils (0.08' millimeters) thick is secured to adhesive 22, coated tape 24 at ground contacting portion 18. Preferably, metallic foil 26 is coated with an electrically conductive adhesive 27, so that ground contacting portion 18 of electrically conductive strap 10 may be secured and electrically coupled to suitable electrical ground. An example of a copper metal coated with an electrically conductive adhesive which may be utilized for metallic foil 26 and electrically conductive adhesive 27 is Scotch Brand 1181 tape available from Minnesota Mining and Manufacturing Company, St. Paul, Minn. Other mechanisms for coupling ground contacting portion 18 to electrical ground are contemplated by the present invention, including using a separate ground coupled to metallic foil 26 with an alligator clip or, perhaps, even coupled directly to elongate strip of electrically conductive material 20 at ground contacting portion 18 without the use of metallic foil 26. Optionally, electrically conductive strap 10 may be supplied with a liner 28 (removed from FIG. 2) to protect adhesive 22 and adhesive 27 before use. Alternatively, electrically conductive body strap 10 may be stored in a rolled up form as in a roll of tape to be unwound at the time of use and, hence, in this application no liner 28 would be required to cover adhesive 22 but still would be preferred to cover adhesive 27, if used.

In operation the electrically conductive body strap 10 of FIGS. 2 and 3 would be utilized by wrapping the body contacting portion 14 around the wrist of the user securing it to the wrist by adhesive 22 on adhesive coated tape 24. Secured in this manner, the elongate strip of electrically conductive material 20 directly contacts the wrist providing an electrical contact to the body of the wearer. At the ground contacting portion 18, the elongate strip of electrically conductive material 20 also directly contacts foil 26. Ground contacting portion 18 may then be secured directly to electrical ground or may be connected to another electrical ground wire (not shown). As for example, with an alligator clip. In a preferred embodiment, adhesive coated tape 24 is a Micropore tape available from Minnesota Mining and Manufacturing Company, St. Paul, Minn. In a preferred embodiment, a suitable liner 28 may be any of a variety of commerically available release liners such as Akrosil silicone coated paper release liner available from Akrosil Corp., Menasha, Wis.

FIG. 4 illustrates a bottom view of an alternative embodiment of the electrically conductive body strap 10A of the present invention. The body contacting portion 14 and ground contacting portion 18 of the electrically conductive body strap 10A are similar to the corresponding portions of the electrically conductive body strap 10 illustrated in FIGS. 2 and 3 but without electrically conductive adhesive 27 and release liner 28. However, lead portion 16 of electrically conductive body strap 10A contains only the elongate strip of electrically conductive material 20. Adhesive coated tape 24 is only contained in the body contacting portion 14 and in ground contact portion 18. In this embodiment of electrically conductive body strap 10A, a strip of electrically conductive material 20 must be mechanically continuous through said lead portion 16 since the elongate strip of electrically conductive material 20 and the lead portion 16 provides not only the electrical integrity of the electrically conductive body strap 10A but also the physical mechanical integrity.

FIG. 5 illustrates a sectional view of an alternative embodiment of an electrically conductive body strap 10B. The body contacting portion 14 and ground contacting portion 18 of the electrically conductive body strap 10B of FIG. 5 are identical to the corresponding portions of the electrically conductive body strap 10A illustrated in FIG. 4. In lead portion 16, however, the electrically conductive body strap 10B contains additional components. The electrically conductive body strap 10B still has an elongate strip of electrically conductive material 20 contacting an adhesive 22 coated tape 24 continuous through the body contacting portion 14, lead portion 16 and grounding portion 18. Also contained in ground portion 18 is metallic foil 26 secured on both sides of elongate strip of electrically conductive material 20 by the adhesive 22 of tape 24. In the lead portion 16 of the electrically conductive body strap 10B, is another adhesive 30 coated tape 32 applied to the opposite side of the elongate strip of electrically conductive material 20 that adhesive 22 coated tape 24 is applied. Also illustrated in FIG. 5 is the possibility that the elongate strip of electrically conductive material 20 may be divided into separate discrete portions. That is, in the embodiment illustrated in FIG. 5, the elongate strip of electrically conductive material 20 does not need to be continuous along the entire length of electrically conductive strap 10B. In this embodiment, the elongate strip of electrically conductive material 20 is formed from a first piece 34 at the body contacting portion 14 where it overlaps and electrically connects to a second piece 36 extending through lead portion 16 and ground contacting portion 18. The electrically conductive body strap 10B may be advantageous to be used in some situations where it is not desirable to have the adhesive 22 exposed in the lead portion 16.

FIG. 6 illustrates an electrically conductive body strap 10C which is an alternative solution to having an electrically conductive body strap with tapes 24 and 32 applied to both sides of the conductive strip 20 to eliminate the exposure of adhesive 22 along the lead portion 16 of electrically conductive body strap 10B illustrated in FIG. 5. In the electrically conductive body strap 10C illustrated in FIG. 6 only one adhesive 22 coated tape 24 is utilized. In body contacting portion 14, the tape 24 is left flat so that the tape 24 may be utilized to adhesively secure the electrically conductive body strap 10C to a body. In lead portion 16, tape 24 is folded over the bottom side of the elongate strip of electrically conductive material 20 in order to not allow adhesive 22 to be exposed in lead portion 16.

FIG. 7 illustrates an alternative embodiment of an electrically conductive strap 10D. Electrically conductive strap 10D as does electrically conductive body strap 10A of FIG. 4 has only an elongate strip of electrically conductive material 20 in lead portion 16. In body contacting portion 14 of electrically conductive body strap 10D, an electrically conductive adhesive 38 supplied to one side of the elongate strip of electrically conductive material 20. Electrically conductive adhesive 38 is covered by protective release liner 40. When electrically conductive body strap 10D is ready to be utilized, release liner 40 is removed and the strap 10D is secured to the body by electrically conductive adhesive 38 since electrically conductive adhesive 38 is transversely electrically conductive, the adhesive 38 also provides electrical contact from the elongate strip of electrical lead conductive material 20 to the body being contacted. A suitable adhesive to be utilized as electrically conductive adhesive 38 is, for example, a solvent based acrylate adhesive containing silver particles about 3 mils (0.76 mm) in diameter which is coated through a knife coater at about 12 mils (3.05 mm) thickness. The coated adhesive is heated to drive off the solvent resulting in an adhesive layer of about 1.5 mils (0.38 mm) in thickness. Note that the silver particles are larger than the thickness of the resulting adhesive giving the layer is needed electrical conductivity. An adhesive similar to this but which has been coated on aluminum is available as X1170 foil tape from Minnesota Mining and Manufacturing Company, St. Paul, Minn. Electrically conductive adhesive 38 may also be utilized at ground contacting portion 18 to secure foil 26 to the elongate strip of electrically conductive material 20 at the ground contacting portion 18. Alternatively, electrically conductive adhesive 38 may be used at ground contacting portion 18 without the use of foil 26 to secure the ground contacting portion 18 to a suitable electrical ground.

FIGS. 8 and 9 illustrate an alternative embodiment of an electrically conductive body strap 10E. Body contacting portion 14 and ground contacting portion 18 of the electrically conductive body strap 10E are identical to the corresponding portions of the electrically conductive body strap 10 illustrated in FIGS. 2 and 3. In lead portion 16 of electrically conductive body strap 10E, a discrete portion is shown having a built in electrical resistance 42. In electrically conductive body straps 10E which are adapted to be applied to the body of a person it is desirable as a safety measure to provide a degree of electrical resistance along the length of the strap 10E usually on the order of approximately 1 megohm. In order to ensure that if the ground contacting portion 18 of the electrically conductive body strap 10E accidentally contacts a high voltage source that resistance 42 will limit the current flowing through the electrically conductive body strap 10E and potentially harming the wearer of the strap 10E. In some instances it is desirable to provide a discrete, rather than continuous, electrical resistance 42. The provision of a discrete resistance 42 allows the electrically conductive body strap 10E to be checked visually and electrically to confirm that the electrical resistance 42 is in place and is operable. The discrete resistance 42 also protects against accidental contact of the electrically conductive body strap to a high voltage source anywhere along the lead portion 16 toward the ground contacting portion 18. With a discrete resistance 42 the resistance would still be intact as opposed to a continuous resistance system in which a proportional decline in protection would occur as the point of contact to the high voltage source moved closer to the body contacting portion 14. Of course, it is recognized that in certain installations little or no discrete electrical resistance 42 may be required or desired. Discrete electrical resistance 42 is formed by providing an area of decreased cross-section of the elongate strip of electrical conductive material 20. As can be seen more clearly in FIG. 9, this decreased cross-section is provided by dimpling or making grooves through the transverse direction of the elongate strip of electrically conductive material 20 in order to provide a higher resistance. It is apparent that as the grooves are made deeper or greater in number, the value of the electrical resistance 42 provided will be increased.

While much of the discussion of the use of an electrically conductive body strap 10 has focused on the straps 10 use as a wrist strap to prevent the electrostatic charging of the body of a person who in turn may come in contact with an electrostatic sensitive article, it is to be recognized and understood that the body being contacted by the body contacting portion 14 may be an inanimate object, e.g., the case of computer, in which it is desired to prevent or eliminate the possibility of dangerous buildups of electrostatic charges. Thus, while primarily operable as a wrist strap, the electrically conductive body strap of the present invention may be utilized both for inanimate objects and for contacting other portions of the body as, for example, ankles.

Thus, there has been shown and described a novel, disposable electrically conductive body strap. It is to be recognized and understood, however, that various changes, modifications and substitutions in the form and of the details of the present invention may be made by those skilled in the art without departing from the scope of the following claims.

I claim:

1. An electrically conductive strap having a distal end adapted to be secured to an object and having a proximate end adapted to be coupled to electrical ground, comprising:
   an elongate strip of electrically conductive material, said material being flexible in at least one dimension, said material having an object contacting portion at said distal end and having a lead portion between said distal end and said proximate end and having a ground contacting portion at said proximate end;
   securing means affixed to said object contacting portion of said material for being able to adhesively secure said material to said object, with said material in electrical contact with said object; and
   ground contacting means at said ground contacting portion of said material for being able to be coupled to electrical ground.

2. An electrically conductive strap as in claim 1 wherein said elongate strip of electrically conductive material is substantially continuous and of the same type of material along said object contacting portion and said lead portion.

3. An electrically conductive strap as in claim 2 wherein said elongate strip of electrically conductive material is an electrically conductive plastic.

4. An electrically conductive strap as in claim 3 wherein said elongate strip of electrically conductive material is constructed from a carbon loaded plastic.

5. An electrically conductive strap as in claim 4 wherein said carbon loaded plastic is a carbon loaded polyethylene.

6. An electrically conductive strap as in claim 2 wherein said elongate strip of electrically conductive material incorporates a resistance means in said lead portion for providing a discrete location which has a higher value of electrical resistance per unit length than the value of the electrical resistance per unit length of the remainder of said elongate strip of electrically conductive material.

7. An electrically conductive strap as in claim 6 wherein said resistance means comprises a section of reduced cross-section of said elongate strip of electrically conductive material.

8. An electrically conductive strap as in claim 1 wherein said elongate strip of electrically conductive material at said object contacting portion is a metallic coated plastic film.

9. An electrically conductive strap as in claim 8 wherein said elongate strip of electrically conductive material is a carbon loaded plastic at said lead portion.

10. An electrically conductive strap as in claim 9 wherein said elongate strip of electrically conductive material is a metallic pad at said ground contacting portion.

11. An electrically conductive strap as in claim 1 wherein said securing means comprises:
    a protective web positioned over said object contacting portion of said elongate strip of electrically conductive material, said web being wider than the width of said elongate strip of electrically conductive material; and
    an adhesive layer securing said protective web and said object contacting portion of said elongate strip of electrically conductive material together, said adhesive layer be capable of securing said protective web to said object and thereby securing said elongate strip of electrically conductive material in electrical contact with said object.

12. An electrically conductive strap as in claim 11 wherein said ground contacting means comprises a metallic pad mechanically and electrically affixed to said elongate strip of electrically conductive material at said ground contacting portion.

13. An electrically conductive strap as in claim 1 wherein said securing means comprises a layer of conductive adhesive applied to said object contacting portion of said material.

14. An electrically conductive body strap having a distal end adapted to be secured to a body and having a proximate end adapted to be coupled to electrical ground, comprising:
    an elongate strip of electrically conductive material being flexible in at least one dimension, said material having a body contacting portion at said distal end, a lead portion between said distal end and said proximate end and having a ground contacting portion at said proximate end;
    a first adhesive coated tape having a width greater than the width of said body contacting portion of said material, said adhesive coated tape being applied, adhesive coated side toward said material, to said body contacting portion of said material;
    whereby said body contacting portion may be secured to said body and said ground contacting portion may be secured to electrical ground.

15. An electrically conductive body strap as in claim 14 wherein said elongate strip of electrically conductive material comprises an electrical conductor in a flat strip.

16. An electrically conductive body strap as in claim 15 wherein said first adhesive coated tape is applied, adhesive coated side toward said material, to said lead portion of said material.

17. An electrically conductive body strap as in claim 16 in which said first adhesive coated tape in said lead portion is at least twice the width of said electrically conductive material at each corresponding location along said lead portion, said first adhesive coated tape being folded over and applied to both sides of said electrically conductive material in said lead portion.

18. An electrically conductive body strap as in claim 15 wherein said elongate strip of electrically conductive material incorporates a resistance means in said lead portion for providing a discrete location which has a higher value of electrical resistance per unit length than the value of the electrical resistance per unit length of the remainder of said elongate strip of electrically conductive material.

19. An electrically conductive body strap as in claim 18 wherein said resistance means comprises a section of reduced cross-section of said elongate strip of electrically conductive material.

20. An electrically conductive body strap as in claim 16 which further comprises a second adhesive coated tape applied, adhesive coated side toward said material, to both sides of said material along said lead portion of said material.

21. An electrically conductive body strap as in claim 15 wherein said elongate strip of electrically conductive material at said body contacting portion comprises a metallic coated plastic film.

22. An electrically conductive body strap as in claim 21 wherein said elongate strip of electrically conductive material comprises an electrically conductive plastic.

23. An electrically conductive body strap as in claim 22 wherein said elongate strip of electrically conductive material is a carbon loaded plastic at said lead portion.

24. An electrically conductive body strap as in claim 23 wherein said elongate strip of electrically conductive material is a metallic pad at said ground contacting portion.

25. An electrically conductive body strap as in claim 15 wherein said elongate strip of electrically conductive material comprises an electrically conductive plastic.

26. An electrically conductive body strap as in claim 25 wherein said elongate strip of electrically conductive material is constructed from a carbon loaded plastic.

27. An electrically conductive body strap as in claim 26 wherein said carbon loaded plastic is a carbon loaded polyethylene.

28. An electrically conductive body strap as in claim 14 which further comprises a removeable liner applied to said first adhesive coated tape at said body contacting portion of said material covering said electrically conductive material.

29. An electrically conductive body strap as in claim 14 wherein said first adhesive coated tape is a nonwoven tape coated with an acrylate adhesive.

* * * * *